United States Patent [19]

Daniels

[11] Patent Number: 4,623,726

[45] Date of Patent: Nov. 18, 1986

[54] METHOD FOR OXIDIZING ALKYL GROUPS ON PYRIDINE, QUINOLINE AND BENZENE RING COMPOUNDS TO CARBOXYLIC ACIDS UNDER BASIC CONDITIONS

[75] Inventor: William A. Daniels, Belle Mead, N.J.

[73] Assignee: American Cyanamid Company, Stamford, Conn.

[21] Appl. No.: 485,769

[22] Filed: Apr. 18, 1983

[51] Int. Cl.$^4$ ............... C07D 215/54; C07D 213/807; C07C 51/16

[52] U.S. Cl. .................................. 546/168; 546/320; 562/409

[58] Field of Search ................. 546/168, 320; 562/409

[56] References Cited

U.S. PATENT DOCUMENTS

| | | | |
|---|---|---|---|
| 2,513,099 | 6/1950 | Mueller | 546/320 |
| 2,515,593 | 7/1950 | Engel et al. | 546/320 |
| 2,793,213 | 5/1957 | Mueller | 546/320 |

Primary Examiner—Glennon H. Hollrah
Assistant Examiner—D. B. Springer
Attorney, Agent, or Firm—Estelle J. Tsevdos

[57] ABSTRACT

There is provided a novel process for the preparation of carboxylic acids from alkyl groups under basic conditions utilizing oxides of copper, cobalt and silver.

14 Claims, No Drawings

METHOD FOR OXIDIZING ALKYL GROUPS ON PYRIDINE, QUINOLINE AND BENZENE RING COMPOUNDS TO CARBOXYLIC ACIDS UNDER BASIC CONDITIONS

The invention herein described relates to a method for the preparation of various carboxylic acids. The method involves the use of various oxides of copper, cobalt or silver under basic conditions to prepare carboxylic acids from alkyl groups. The higher oxidation states of copper, cobalt, or silver [i.e., those greater than Cu(II), Co(II) or Ag(I)], generated by either chemical or electro-chemical methods, are suitable for oxidizing alkyl groups to carboxylic acids under basic conditions. The method of the invention is conveniently suitable for the oxidation of methyl groups to carboxylic acids.

By way of background, it is well-known that various carboxylic acids (i.e., 2,3-pyridinedicarboxylic acid) are susceptible to decarboxylation under common methods of preparation. While there are numerous procedures available for oxidizing methyl groups to carboxylic acids, most of these methods are conducted under acidic conditions where sensitivity to decarboxylation can be a problem. Many acids, such as 2,3-pyridinedicarboxylic acid, are prone to decarboxylation under such conditions.

In light of the foregoing summary of some demands and limitations of conventional methods for the oxidation of alkyl groups to carboxylic acids, an improved method for producing such carboxylic acids is highly desirable. An object of this invention is to provide a new and useful method for the production of various carboxylic acids under basic conditions by the oxidation of alkyl groups. This object is manifest in the following description and particularly delineated in the appended claims.

Compounds comprised of higher oxidation states of copper [>Cu(II)], cobalt [>Co(II)] or silver [>Ag(II)] are particularly well-adapted for oxidizing alkyl groups to carboxylic acids under basic conditions. Oxidants suitable for use in the method of the invention are represented by formula I below:

$$X_mY_n \quad (I)$$

wherein X is copper, cobalt or silver; Y is oxygen; m is 1 or 2; n is an integer of 1 to 6; and n≧m. Among the formula-I oxidants that can be utilized in the practice of the invention are: $Co_2O_3$, $Cu_2O_3$, and $Ag_2O_2$. The compound 2,3-pyridinedicarboxylic acid, which is notably sensitive to decarboxylation, may be prepared quite satisfactorily by the method of the present invention.

It has been unexpectedly found that compounds containing copper, cobalt, or silver in higher oxidation states may conveniently be prepared with oxidants such as chlorine or hypochlorite and utilizing salts such as CuO, Cu(OH)$_2$, Cu(NO$_2$)$_2$.6H$_2$O, Cu(NO$_2$)$_2$.3H$_2$O, CuO and Ag$_2$O. Such oxidants may be utilized for a full range of oxidation reactions under both steady-state continuous conditions and batch conditions, and may also be recycled. The reaction may be illustrated as follows:

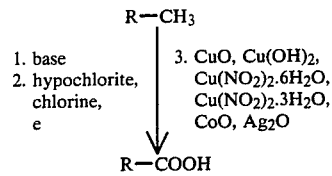

wherein R is alkyl, arylalkyl, or heteroarylalkyl.

The process of the present invention is useful in preparing 2,3-pyridine and 2,3-quinolinedicarboxylic acids which are intermediates in the preparation of the herbicidally effective agents, 2-(4,4-disubstituted-5-oxo (or thiono)-2-imidazolin-2-yl)nicotinic acids and 3-quinolinecarboxylic acids. Further, these heterocyclic aromatic acids also are intermediates in the synthesis of pharmaceuticals, such as vitamins, coenzymes and alkaloids.

Illustrative of the above process, 5 g of pulverized cupric oxide is added to a solution of 10 g 2-methyl-3-quinolinecarboxylic acid in 100 ml of 15% aqueous sodium hydroxide. The solution is heated to 75° C. and 200 ml of 15.5% aqueous sodium hypochlorite is added over 30 minutes. The reaction mixture is stirred at 75° C. for 18 hours and an additional 200 ml aliquot of sodium hypochloride is added. After three additional hours, the mixture is filtered, chilled to 15° C., and acidified to pH 3. The product, 2,3-quinolinedicarboxylic acid, is isolated in 90% yield. Alternatively, 10 g of 2-methyl-3-quinolinecarboxylic acid and 100 ml of water is placed in a reactor. The pH of the mixture is adjusted to 10 and 20 g of cupric hydroxide is added. The mixture is first warmed to 85° C. for one hour to convert the cupric hydroxide to its oxide, and then cooled to 55° C. An automatic pH controller is set to maintain the pH above 10. Chlorine gas is then introduced at the rate of approximately 2 g/hr for 24 hours. The reaction is cooled and the product precipitates after the pH is adjusted to 3. A 65% yield of 2,3-quinolinedicarboxylic acid is obtained.

The higher oxides of copper, cobalt or silver oxidants may be formed on an electrode surface by slaking the electrode in aqueous hydroxide, and then applying a voltage below that at which oxygen evolution occurs.

EXAMPLE 1

Copper oxidation of 2-methyl-nicotinic acid 20 g of cupric hydroxide is added to a stirred solution of 25 ml of a 50% aqueous solution of NaOH and 25 ml H$_2$O. The solution is heated to 55° C. After 15 minutes, 8.5 g (0.62 mol) of 2-methyl-3-nicotinic acid is added. A pH controller is set to maintain the pH of the reaction mixture above 10 by incremental addition of 50% aqueous NaOH. Chlorine gas is then introduced at the rate of 10 g in one hour, followed by 1 g per hour thereafter until a total of about 28.4 g Cl$_2$ is added. The reaction mixture is then filtered while hot, chilled to 15° C., acidified to pH 3, and filtered to give 6.71 g (64.8% yield) of 2,3-pyridinedicarboxylic acid after drying. The reaction is illustrated as follows:

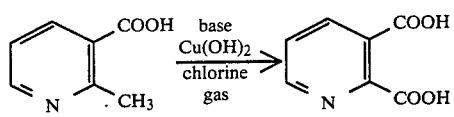

EXAMPLE 2

Copper oxidation of 2-methyl-3-quinolinecarboxylic acid

A solution containing 3.8 g of pulverized copper oxide, 7.5 g water, 3 g of 50% aqueous NaOH and 1.0 g (4.87 mol) 2-methyl-3-quinolinecarboxylic acid is prepared at 70° C. with stirring. 20 ml of 15% aqueous sodium hypochlorite solution is added and the reaction mixture is stirred for 18 hours. A second 20 ml aliquot of hypochlorite is added and the reaction mixture is stirred an additional three hours before being cooled, filtered and analyzed by high performance liquid chromatography. The aqueous solution contains 0.97 g of 2,3-quinolinedicarboxylic acid representing a 92% yield. The reaction is illustrated as follows:

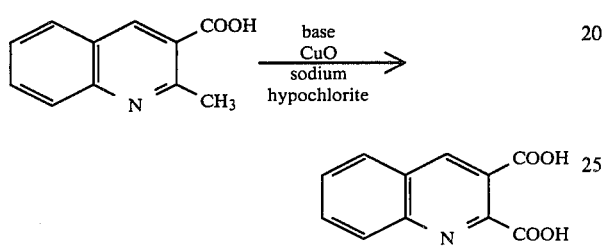

EXAMPLE 3

Electrolytic copper oxidation of 2-methyl-3-quinolinecarboxylic acid

A solution of 7.5 g (0.040 mol) of 2-methyl-3-quinolinecarboxylic acid in 100 ml of 15% aqueous sodium hydroxide is added to a reactor fitted with a copper anode (4×10×0.025 cm) and a nickel cathode (4×10×0.0175 cm). The solution is warmed with stirring to 40° C. A current of 10 mA at 1.47 v is applied for 24 hours. The assayed reaction mixture contains 0.4 g of 2,3-quinolinedicarboxylic acid representing a 5% yield. The reaction is illustrated as follows:

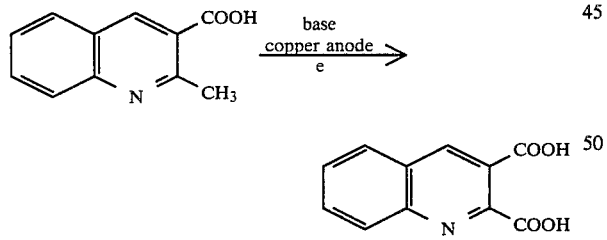

EXAMPLE 4

Electrolytic oxidation of 2-methyl-3-quinolinecarboxylic acid

A solution of 7.5 g (0.040 mol) of 2-methyl-3-quinolinecarboxylic acid in 100 ml of 15% aqueous sodium hydroxide is placed in a reactor fitted with a cobalt anode (4×10×0.25 cm) and a nickel cathode (4×10×0.0175 cm). The solution is heated to 95° C. and a current of 2 mA and 1.47 v is applied. After 600 hours, the reaction mixture is cooled to 15° C. and acidified to pH 3. The product, 2,3-quinolinedicarboxylic acid, is filtered and dried to constant weight. A yield of 1.4 g of product is obtained representing a 90% yield. The reaction is illustrated as follows:

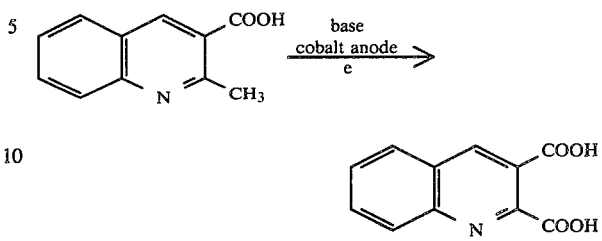

EXAMPLE 5

Copper oxidation of 2-methyl-3-quinolinecarboxylic acid

To a reactor is added 4.03 g (18.9 mmol) of 2-methyl-3-quinolinecarboxylic acid hydrochloride and 40 ml water. The pH is adjusted to pH 10 and 16.0 g cupric hydroxide is added. The solution is warmed to 85° C. for 60 minutes; then cooled and held at 55° C. A pH controller is set to maintain the pH above 10 by the incremental addition of aqueous 50% sodium hydroxide solution. Chlorine gas is introduced at approximately 1 g/hr to give a total of 20 g after 21 hours. The reaction mixture is filtered and analyzed; 2.82 g of 2,3-quinolinedicarboxylic acid is obtained. The reaction is illustrated as follows:

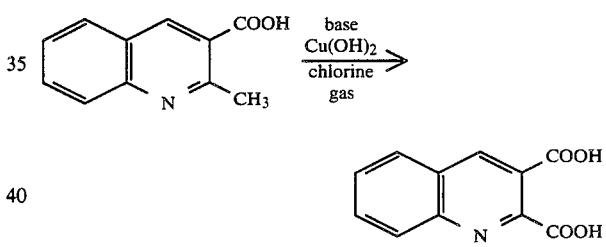

EXAMPLE 6

Continuous copper oxidation of 2-methyl-3-quinolinecarboxylic acid

A jacketed 1×50 cm column is packed with copper oxide wire (1 mm dia×5 mm length). The column temperature is set at 75° C. by use of an external thermostatted bath connected to the column jacket. A solution of 1.0 g (4.7 mmol) of 2-methyl-3-quinolinecarboxylic acid, 8 ml water, and 2 g of 50% aqueous sodium hydroxide is introduced to the column at a rate of 0.054 ml/minute simultaneously with 15 g (39.1 mmoles) of 15.5% aqueous sodium hypochlorite at a rate of 0.10 ml/minute. The reaction mixture exiting the column is assayed to contain 17.0% of unreacted 2-methyl-3-quinolinecarboxylic acid and 80.6% of the product 2,3-quinolinedicarboxylic acid. The reaction is illustrated as follows:

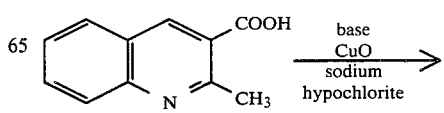

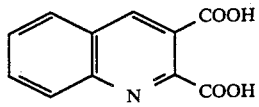

EXAMPLE 7

Copper oxidation of o-toluic acid

To a reactor is added 25 ml of H₂O, 25 ml of 50% NaOH, and 20 g of cupric hydroxide with stirring. The temperature is brought to 55° C. After 15 minutes, 6.8 g (0.05 mol) o-toluic acid is added to this solution. A pH controller is set to maintain the pH above 10 by incremental addition of 50% aqueous NaOH. Chlorine gas is introduced at a rate of 0.16 g/min for the first 85 minutes, and then at 0.03 g/min to give a total of 25 g of chlorine. The solution is filtered and the filtrate chilled to 15° C. The pH is adjusted to 3 with 37% HCl. The product is filtered and dried to yield 4.11 g phthalic acid. This represents a product yield of 49.5%. The reaction is illustrated as follows:

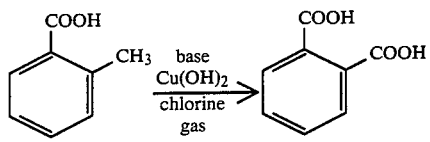

EXAMPLE 8

Copper oxidation of 3-(3-pyridinyl)propanol

To a reactor is added 25 ml of 50% aqueous NaOH, sufficient water to bring the volume to 50 ml, and 6.9 g (0.05 mol) of 3-(3-pyridinyl)propanol. The solution is brought to 55° C. and 20 g of cupric hydroxide is added. A pH controller is set to maintain the pH above 10 by the incremental addition of 50% aqueous NaOH. After 5 minutes, chlorine is introduced at approximately 1 g/hr. After 48 hours and about 32 g of chlorine have been added, the reaction mixture is assayed for the appearance of product by high performance liquid chromatography. A yield of 5.96 g of nicotinic acid is obtained. This represents a product yield of 97%. The reaction is illustrated as follows:

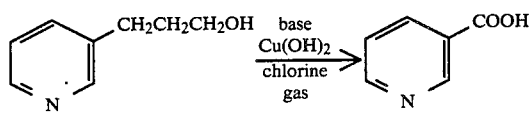

EXAMPLE 9

Copper oxidation of 1,2,4-trimethylbenzene

To a reactor is added 25 ml of 50% aqueous NaOH and sufficient water to total 50 ml. The solution is heated to 55° C. and 20 g of cupric hydroxide is added, followed by 6.1 g (0.05 mol) of 1,2,4-trimethylbenzene. The temperature of the solution is adjusted to 70° C. A pH controller is set to maintain the pH above 10 by the incremental addition of 50% aqueous NaOH. Chlorine gas is then introduced at the rate of approximately 1 g/hr for 62 hours to a total of 43.8 g of chlorine. The reaction mixture is filtered, chilled to 15° C. and acidified with 37% HCl to pH 2. The product is collected by filtration, dried and analyzed by high performance liquid chromatography. A yield of 2.48 g of 1,2,4-benzenetricarboxylic acid is obtained. This represents a product yield of 23%. The reaction is illustrated as follows:

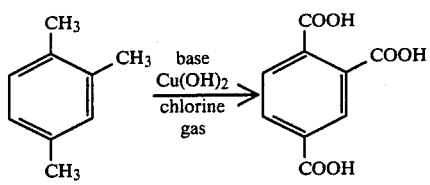

EXAMPLE 10

Copper oxidation of 2,3-lutidine

To a stirred mixture of 20 g of cupric hydroxide, is added 5.5 g (0.05 mol) of 2,3-lutidine, 25 g of 50% aqueous NaOH, and sufficient water to bring the volume to 50 ml. The reaction mixture is heated at 70° C. until cupric oxide formation is visually complete, then cooled to 55° C. A pH controller is set to maintain the pH of the mixture above 10 by the incremental addition of 50% aqueous NaOH. Chlorine gas is then introduced at the rate of approximately 3 g/hr. After 14 g (19 mmol) of chlorine has been added, the solution is assayed by high performance liquid chromatography to contain 0.45 g of 2,3-pyridinedicarboxylic acid (representing a 5% yield) and 1.38 g of 2-methyl nicotinic acid (representing a 14.7% yield). The reaction is illustrated as follows:

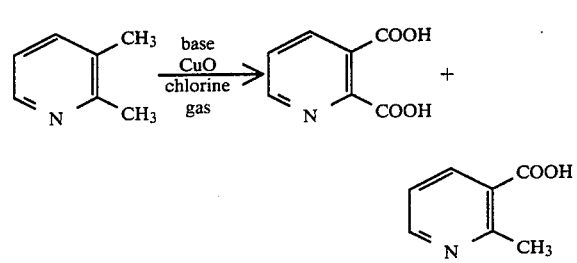

EXAMPLE 11

Silver Oxidation of 2-methyl-3-quinolinecarboxylic acid

To a reactor is added 30 ml of H₂O, 15 g of 50% aqueous NaOH, and 5.0 g (22.3 mmol) of 2-methyl-3-quinolinecarboxylic acid hydrochloride. The solution is heated to 65° C. and 5.0 g (40.4 mmol) Ag₂O₂ is added with stirring. After 20 hours, the solution is analyzed by high performance liquid chromatography. A product of 1.3 g of 2,3-quinolinedicarboxylic acid (representing a 26.9% yield) and 3.36 g of 2-methyl-3-quinolinecarboxylic acid starting material (representing 67.2% recovery) are present. The reaction is illustrated as follows:

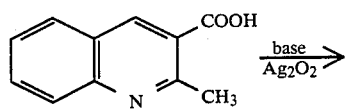

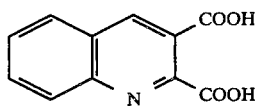

EXAMPLE 12

Cobalt oxidation of 2-methyl-3-quinolinecarboxylic acid

To a reactor is added 30 ml of $H_2O$ and 15 g of 50% aqueous NaOH. The solution is heated to 65° C. and 3.85 g (0.051 mol) of cobalt oxide and 5 g (0.022 mol) of 2-methyl-3-quinolinecarboxylic acid hydrochloride are added with stirring. A chilled solution of 13 g (0.18 mol) of chlorine in 40 g of chlorine in 40 g of 25% aqueous NaOH (~24% aqueous NaOCl) is added over 3 hours. The solution is then stirred for 15 hours and an additional aliquot of 24% aqueous NaOCl (0.36 mol total) is added over 3 hours. After a total of 36 hours, the solution is filtered, chilled to 15° C. and acidified to pH 3. The solid material is removed by filtration. A product of 2.3 g of 2,3-quinolinedicarboxylic acid is obtained. This represents a yield of 77% based on consumed 2-methyl-3-quinolinecarboxylic acid. The reaction is illustrated as follows:

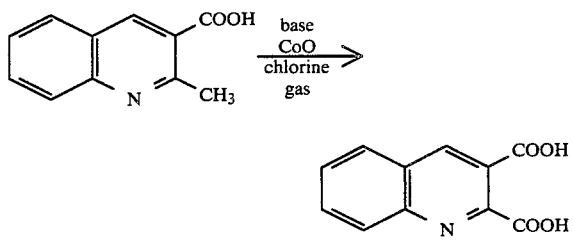

What is claimed is:

1. A method for the oxidation of one or more $CH_3$ groups to a carboxylic acid product, wherein said $CH_3$ group is attached to a pyridine, quinoline or benzene ring compound, said method comprising: reacting said $CH_3$ substituted compound with a hydroxide or oxide of formula (I)

$$X_mY_n \qquad (I)$$

wherein X is copper, cobalt or silver; Y is oxygen or hydroxyl; m is an integer of 1 or 2; n is an integer of 2 to 6; and n>m; with a molar excess of 50% to 250% of an aqueous hypochlorite salt at a temperature of 25° C. to 95° C. at pH>9.

2. A method according to claim 1, wherein said hydroxide or oxide of copper, cobalt or silver is CuO.

3. A method according to claim 2, wherein said $CH_3$-substituted mono-nitrogen heterocyclic ring or benzene ring compound is 2-methyl nicotinic acid; and said carboxylic acid product is 2,3-pyridinecarboxylic acid.

4. A method according to claim 2, wherein said $CH_3$-substituted mono-nitrogen heterocyclic ring or benzene ring compound is 2-methyl-3-quinolinecarboxylic acid; and said carboxylic said product is 2,3-quinolinedicarboxylic acid.

5. A method for the oxidation of one or more $CH_3$ groups to carboxylic acid product, wherein said $CH_3$ group is attached to a mono-nitrogen heterocyclic ring or benzene ring compound, said method comprising: reacting said $CH_3$-substituted mono-nitrogen heterocyclic ring or benzene ring compound with an oxide or hydroxide of formula (I)

$$X_mY_n \qquad (I)$$

wherein X is copper, cobalt or silver; Y is oxygen; m is an integer of 1 or 2; n is an integer of 2 to 6; and n≧m; with 50% to 250% molar excess of chlorine gas; and conducting said reaction at a pH>9.

6. A method according to claim 5, wherein said oxide or hydroxide of copper, cobalt or silver is $Cu(OH)_2$.

7. A method according to claim 6, wherein said $CH_3$-substituted mono-nitrogen heterocyclic ring or benzene ring compound is 2-methyl nicotinic acid; and said carboxylic acid product is 2,3-pyridinecarboxylic acid.

8. A method according to claim 6, wherein said $CH_3$-substituted mono-nitrogen heterocyclic ring or benzene ring compound is 2-methyl-3-quinolinecarboxylic acid; and said carboxylic acid product is 2,3-quinolinedicarboxylic acid.

9. A method according to claim 6, wherein said $CH_3$-substituted mono-nitrogen heterocyclic ring or benzene ring compound is o-toluic acid; and said carboxylic acid product is phthalic acid.

10. A method according to claim 6, wherein said $CH_3$-substituted mono-nitrogen heterocyclic ring or benzene ring compound is 3-(3-pyridinyl)propanol; and said carboxylic acid product is nicotinic acid.

11. A method according to claim 6, wherein said $CH_3$-substituted mono-nitrogen heterocyclic ring or benzene ring compound is 1,2,4-trimethylbenzene; and said carboxylic acid product is 1,2,4-benzenitricarboxylic acid.

12. A method according to claim 6, wherein said $CH_3$-substituted mono-nitrogen heterocyclic ring or benzene ring compound 2,3-lutidine; and said carboxylic acid product is 2,3-pyridinedicarboxylic acid or 2-methyl nicotinic acid.

13. A method according to claim 6, wherein said oxide or hydroxide of XmYn is CoO.

14. A method according to claim 13, wherein said $CH_3$-substituted mono-nitrogen heterocyclic ring or benzene ring compound is 2-methyl-3-quinolinecarboxylic acid; and said carboxylic acid product is 2,3-quinolinedicarboxylic acid.

* * * * *